US00PP36922P2

(12) United States Plant Patent
Erhart

(10) Patent No.: US PP36,922 P2
(45) Date of Patent: Sep. 2, 2025

(54) ***EUPHORBIA* PLANT NAMED 'WALEULITR'**

(50) Latin Name: *Euphorbia martinii*
Varietal Denomination: WALEULITR

(71) Applicant: WALBERTON PLANTS LIMITED, Arundel (GB)

(72) Inventor: Eva Erhart, Worthing (GB)

(73) Assignee: Walberton Plants LTD, Walberton (GB)

( * ) Notice: Subject to any disclaimer, the term of this patent is extended or adjusted under 35 U.S.C. 154(b) by 0 days.

(21) Appl. No.: 19/191,341

(22) Filed: Apr. 28, 2025

(51) Int. Cl.
*A01H 5/02* (2018.01)
*A01H 6/38* (2018.01)

(52) U.S. Cl.
USPC ..... Plt./302

(58) Field of Classification Search
USPC ..... Plt./263.1, 302
See application file for complete search history.

(56) References Cited

U.S. PATENT DOCUMENTS

PP16,930 P2 * 8/2006 Crowther ..... A01H 6/38 Plt./302
PP21,401 P2 * 10/2010 Glenn ..... A01H 5/02 Plt./302

* cited by examiner

*Primary Examiner* — Karen M Redden
(74) *Attorney, Agent, or Firm* — Weatherly IP Solutions, LLC; James M. Weatherly

(57) ABSTRACT

A new cultivar of *Euphorbia* named 'WALEULITR' that is distinguished by compact rounded habit. After the first season of growth, plants of 'WALEULITR' are 15 cm. in height and 20 cm. in diameter. After three years of growth in a larger container or in-ground, plants of 'WALEULITR' are 35 cm. in height and 50 cm. in diameter. 'WALEULITR' exhibits small lime-green cyathia in spring and summer. Each cyathium opens to display shallow cup-shaped lime-green petal-like bracts from whose center a solitary female flower emerges, then bends away and is replaced by four or five male flowers. The female flower is surrounded by lime-green or pink-red horned glands which present as a pink-red eye. 'WALEULITR' is hardy to USDA Zone 6, is drought-tolerant and is suitable for use in containers, rock gardens, and as a groundcover in the landscape.

4 Drawing Sheets

Genus and species: *Euphorbia martinii.*
Variety denomination: 'WALEULITR'.

BACKGROUND

The present invention relates to a new and distinct cultivar of spurge, an ornamental plant that is suitable for use in container, rock garden, or as a groundcover in the landscape. The new invention is known botanically as *Euphorbia martinii*, and will be referred to hereinafter by the cultivar name 'WALEULITR'.

In 2017, the inventor discovered 'WALEULITR' in a greenhouse nursery in Walberton, West Sussex, United Kingdom as a naturally occurring single branch sport on an individual plant of *Euphorbia martinii* 'WALEUTINY' (U.S. Plant Pat. No. 16,930) that was growing in a commercial crop of 'WALEUTINY'. 'WALEULITR' is distinguishable from the parent plant 'WALEUTINY' by foliage color, as follows: the foliage of 'WALEUTINY' is uniformly green throughout the season while the foliage of 'WALEULITR' is mid-green in color in late spring, becoming golden and then bronze in color in late summer and early fall.

The first asexual reproduction of 'WALEULITR' was conducted in 2017 by the inventor in a greenhouse in West Sussex, United Kingdom. The inventor excised the discovered branch sport and made a stem cutting for immediate rooting. Once rooted and grown-on, the inventor carried out further vegetative propagations by stem cuttings. The inventor has determined that the characteristics of the new cultivar 'WALEULITR' has remained stable and fixed, and that it reproduces true to type in successive generations.

SUMMARY OF THE INVENTION

The following traits have been repeatedly observed and represent the distinguishing characteristics of the new *Euphorbia* cultivar named 'WALEULITR'. These traits in combination distinguish 'WALEULITR' from all other existing varieties of *Euphorbia* known to the inventor. 'WALEULITR' has not been tested under all possible conditions and phenotypic differences may be observed with variations in environmental, climatic, and cultural conditions, however, without any variance in genotype.

1. *Euphorbia martinii* 'WALEULITR' exhibits a compact rounded habit, naturally forming a spherical shape with minimal pruning.
2. After the first season of growth, plants of 'WALEULITR' are 15 cm. in height to top of foliage mound, 20 cm. in height to top of flower canopy, and 20 cm. in overall diameter.
3. After three years of growth in a larger container or in-ground, flowering plants of 'WALEULITR' are 23 cm. in height and 50 cm. in diameter.

4. *Euphorbia martinii* 'WALEULITR' exhibits small lime-green flower-like cyathia in spring and summer. Each cyathium opens to display shallow cup-shaped petal-like bracts from whose center a solitary female flower emerges, then bends away and is replaced by four or five male flowers.
5. *Euphorbia martinii* 'WALEULITR' is hardy to USDA Zone 6.
6. *Euphorbia martinii* 'WALEULITR' is suitable for use in container, rock garden, and as a groundcover in the landscape.

BRIEF DESCRIPTION OF THE PHOTOGRAPHS

Figure 1:
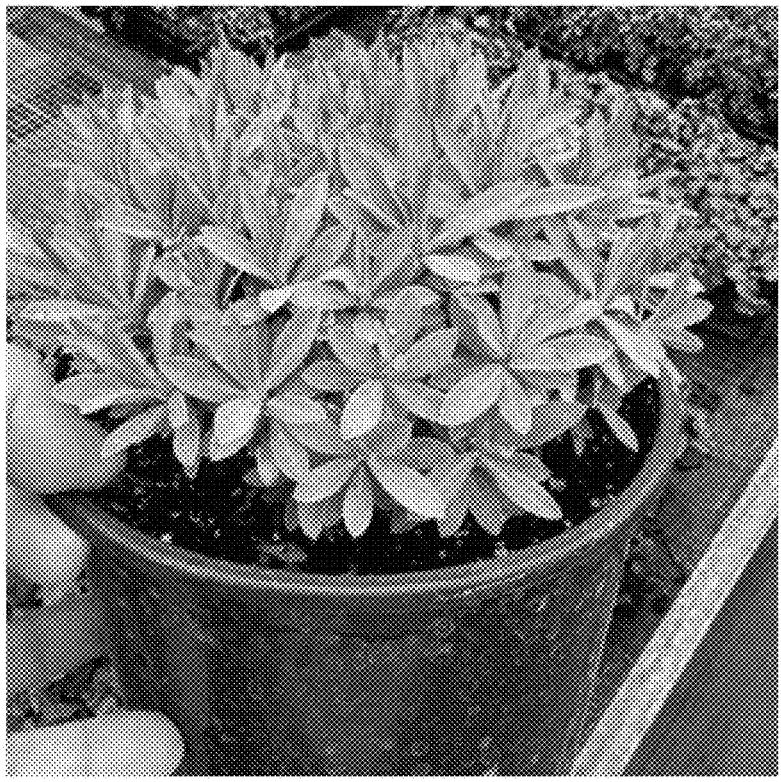
Figure 2:
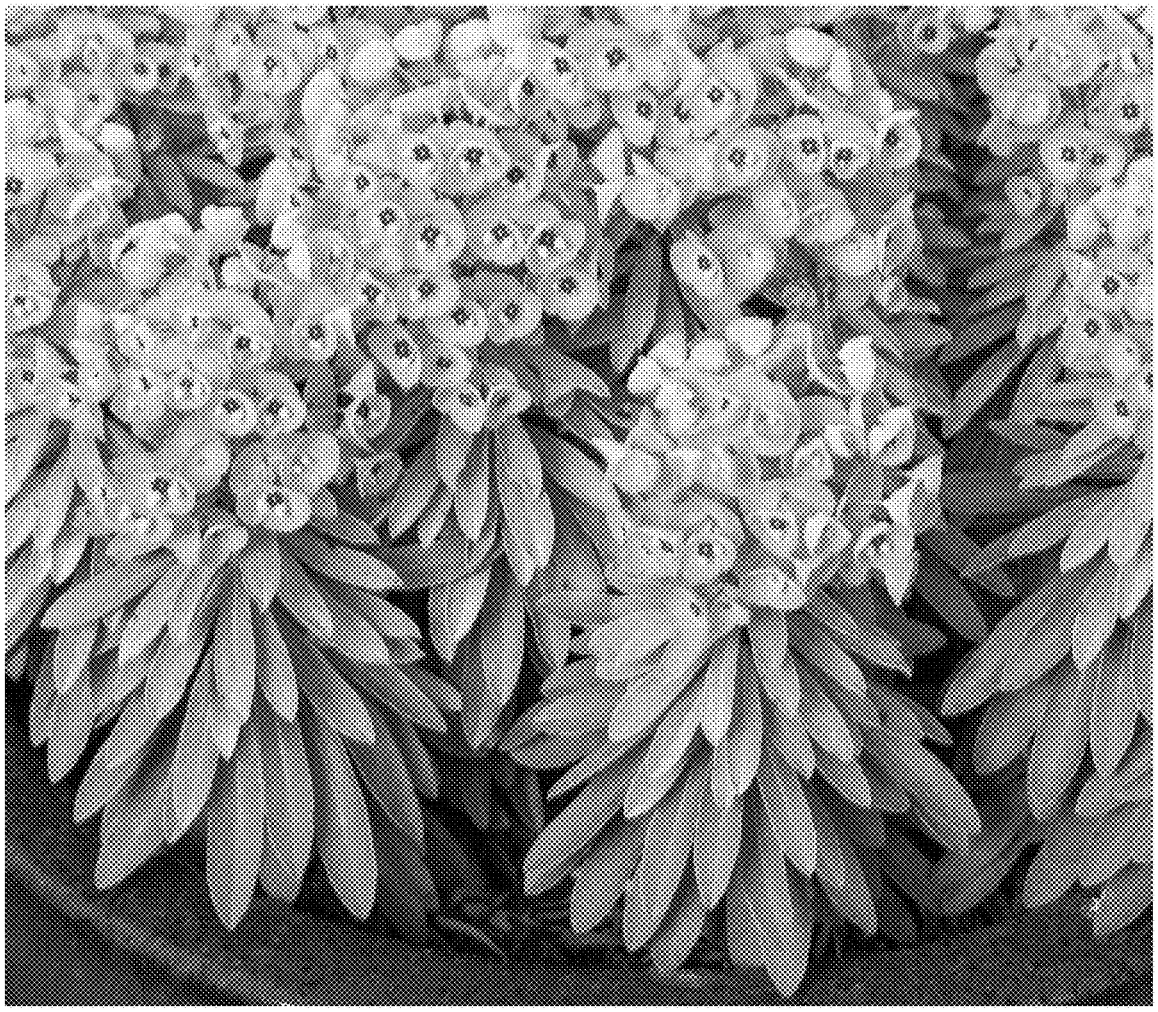
Figure 3:
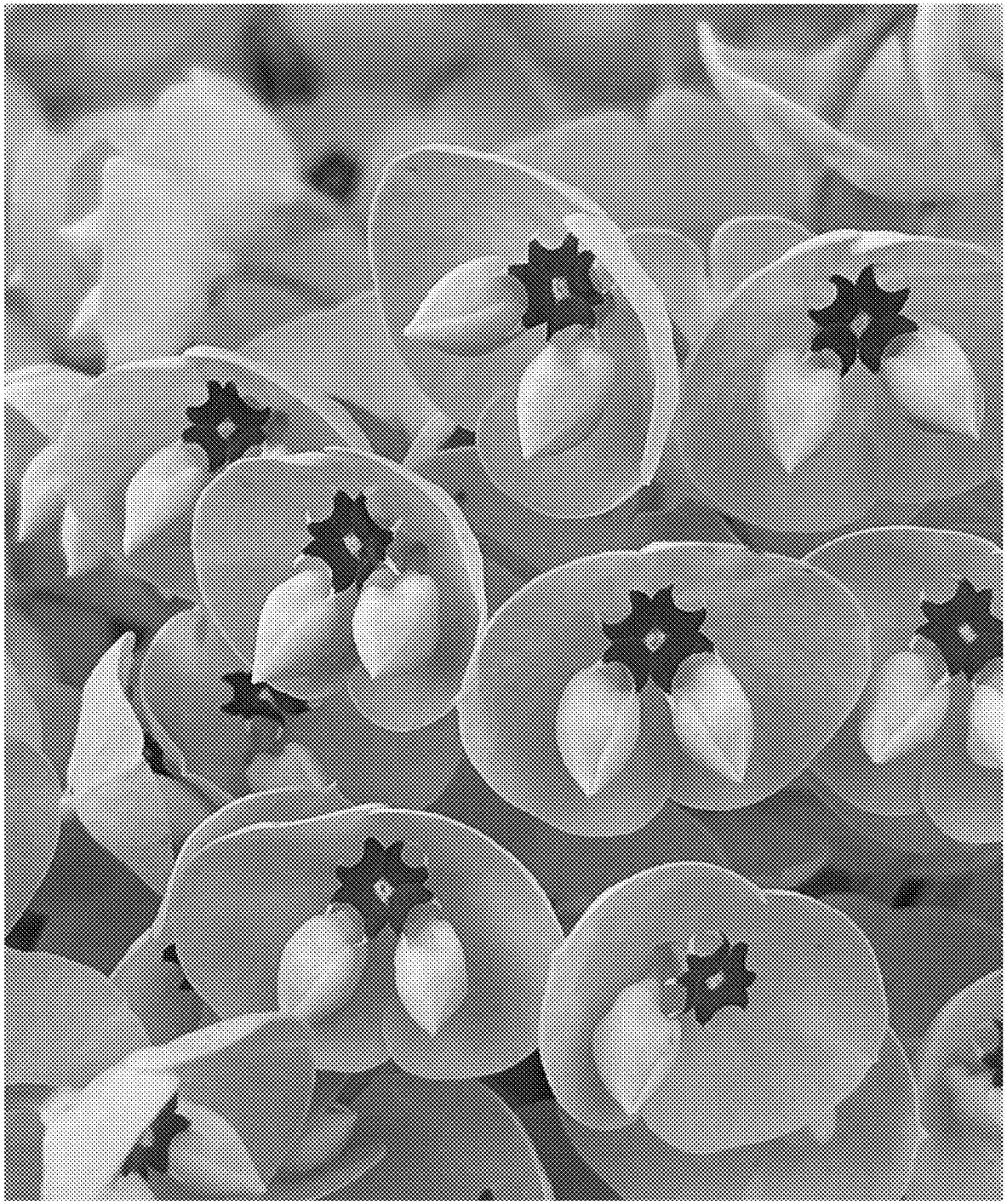

The accompanying color photographs FIG. 1, FIG. 2, and FIG. 3 illustrate the overall appearance of the new *Euphorbia* cultivar 'WALEULITR' showing the colors as true as it is reasonably possible to obtain in colored reproductions of this type. Colors in the photograph may differ from the color values cited in the detailed botanical description, which accurately describe the actual colors of the new variety 'WALEULITR'.

The photograph labeled as FIG. 1 illustrates a one-year-old plant of 'WALEULITR' in its spring foliage.

The photograph labeled as FIG. 2 illustrates an established plant of 'WALEULITR' in its late summer and early fall foliage.

The photograph labeled as FIG. 3 presents a close-up view of the cyathium of 'WALEULITR'.

Figure 4:
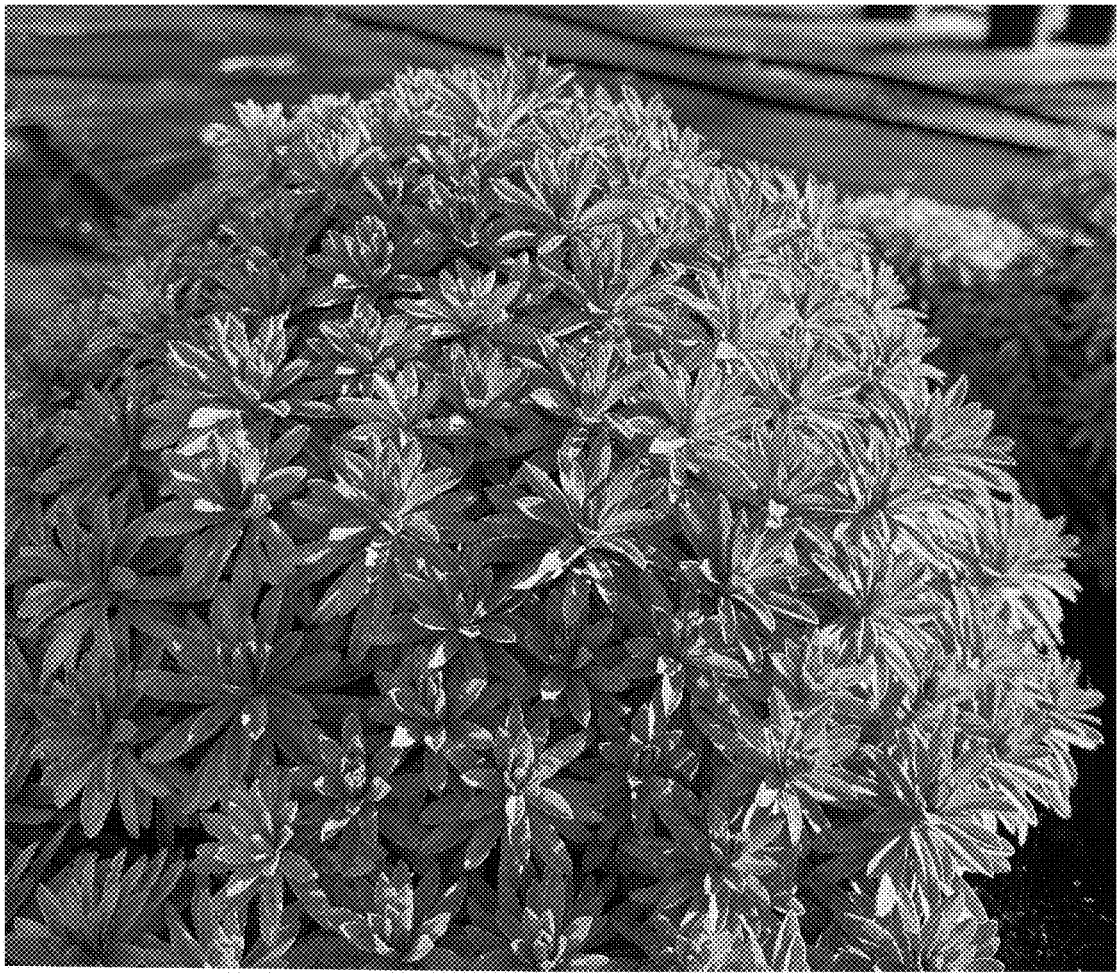

The photograph labeled as FIG. 4 illustrates an established two-year-old plant of 'WALEULITR' with its winter foliage.

The photographs were made from plants grown out of doors in Walberton, West Sussex, United Kingdom. The illustrated plants had not been pruned or treated with any plant growth regulator. The colors in the drawings are as accurate as possible by conventional photography and may appear different from actual colors due to light reflectance.

BOTANICAL DESCRIPTION OF THE PLANT

The following is a detailed botanical description of the new *Euphorbia* cultivar 'WALEULITR'. Observations, measurements, values and comparisons were collected in Santa Barbara, California from 2-litre container plants that were 12-months-old at the time and which had been grown out-of-doors in full sun or, as needed, in light shade. Color determinations are made in accordance with the 2007 edition of the Royal Horticultural Society Colour Chart of London, England, except where general color terms of ordinary dictionary significance are used. The growing requirements of the new variety are similar to the species.

Botanical classification:

*Genus*.—*Euphorbia*.
*Species*.—*martinii*.
*Variety*.—'WALEULITR'.
*Common name*.—Spurge.

Parentage: *Euphorbia* 'WALEULITR' is a naturally occurring single branch sport discovered on an individual plant of the following parent: *Euphorbia martinii* 'WALEUTINY' (U.S. Plant Pat. No. 16,930).

Plant description:

*Commercial classification*.—Perennial or sub-shrub.
*Size*.—Dwarf.
*Asexual propagation method*.—Vegetative tip and stem (internodal) cuttings.
*Rooting habit*.—Fine.
*Time to develop roots*.—2 weeks are needed for roots to develop on an initial cutting.
*Temperature recommended to develop roots*.—18° Centigrade.
*Crop time*.—8 months are needed to produce a finished and flowering plant in a 1-litre container from planting a rooted cutting or young plant.
*Growth habit*.—Compact, naturally branching prolifically.
*Plant shape*.—Ball-shaped.
*Use*.—Ornamental plant suitable for use in container, rock garden, and as a groundcover for the landscape.
*Type*.—Perennial or sub-shrub.
*Vigor*.—Moderate vigor.
*Height of plant* (*after one season*).—15 cm. in height at the top of the foliage and 30 cm. in height at the top of the flowers.
*Width of plant* (*after one season*).—20 cm. in width.
*Cultural requirements*.—Sun or partial shade and well-draining soil. 'WALEULITR' is drought-tolerant.
*Susceptibility to pests*.—Can be affected by aphids (*Aphidae* spp.), red spider mite (*Tetranychus urticae*), and whitefly (order *Trialeurodes*).
*Susceptibility to diseases*.—Can be affected by mildew (*Ascomycete* fungi) or rust diseases (order *Pucciniales*).
*Hardiness*.—At least hardy to USDA Zone 6.
*Special considerations*.—Hazardous sap. All parts exude a cream-white (NN155B) milky sap which, if typical of the genus, is liable to be toxic if ingested or to cause dermal irritation after contact.

Stem:

*Branching habit*.—Central trunk with many branching stems.
*Trunk dimensions*.—2.5 cm. in diameter and 3 cm. in height.
*Trunk shape*.—Cylindrical.
*Trunk surface*.—Pubescent.
*Trunk color*.—Individual colors 183A and 144B are present on an individual trunk.
*Lateral stem color*.—Individual colors 183A and 144B are present on an individual lateral stem.
*Lateral stem shape*.—Cylindrical.
*Lateral stem diameter*.—5 mm. in diameter tapering to 3 mm. close to first leaf pairs.
*Lateral stem length*.—Lateral stem ranges from 12 cm. to 15 cm. in length.
*Lateral stem surface*.—Pubescent.
*Internode length*.—3 mm.

Foliage:

*Type*.—Evergreen.
*Leaf arrangement*.—Opposite pairs arranged spirally.
*Leaf division*.—Simple.
*Leaf shape*.—Narrow, oblanceolate.
*Leaf length*.—Ranges between 6 cm. and 8 cm.
*Leaf width*.—Individual leaf ranges from 5 mm. to 10 mm.
*Leaf apex*.—Apiculate.
*Leaf base*.—Attenuate.
*Quantity of leaves*.—A range of 65-75 leaves per stem.
*Leaf venation pattern*.—Pinnate. Veins very faintly visible except prominent mid-vein of lighter color (adaxial surface only).
*Mid-vein color* (*adaxial surface*).—138C.

*Margin*.—Entire.

*Leaf surface* (*abaxial surface*).—Pubescent.

*Leaf surface* (*adaxial surface*).—Pubescent.

*Leaf appearance* (*adaxial and abaxial surfaces*).—Matte.

*Leaf attachment*.—Sessile.

*Leaf colors* (*spring, first growing season*) *Both surfaces*.—Ranging between yellow-green 153B and N144B.

*Leaf colors* (*late summer and fall*) *Both surfaces*.—Older, lower leaves exhibit spring colors 153B-N144B. Recently emerged uppermost leaves will become grey-range N163B in color, notably in bright fall days and cool nights.

*Leaf fragrance*.—None observed.

Flower:

*Type of inflorescence*.—Cyathium, consisting of cupped petal-like bracts subtending a solitary central pedicellate female flower which ages and bends away to be replaced by four or five male flowers.

*Blooming season*.—Spring and summer.

*Dimensions of individual cyathium*.—8 mm. in height (from bract perimeter to bract base), and 12 mm. in diameter.

*Cyathium arrangement*.—Whorled.

*Number of cyathia per peduncle*.—20-22 cyathia per peduncle.

*Quantity of cyathia per pedicel*.—2.

*Aspect*.—Facing upward and outward.

*Bud* (*closed bracts*) *shape*.—Oval, apex acute, base obtuse.

*Bud dimensions*.—4 mm. in length and 3 mm. in diameter.

*Bud surface*.—Glabrous.

*Bud color*.—145A.

*Peduncle* (*subtends cyathia cluster*).—Dimensions: 9 cm. in length, 4 mm. in diameter. Peduncle color: 145A Peduncle shape: Cylindrical. Peduncle appearance: Semi-glossy. Peduncle surface: Mostly glabrous but with a few hairs.

*Perianth*.—Absent.

*Bracts*.—Number, arrangement: 4 in total as 2 opposite pairs. Shape: Deltoid in adjacent pairs, fused at pair base, otherwise free. Apex: Horned. Color (both surfaces): 144B. Margin: Entire. Apex: Obtuse apex. Base: Truncate.

*Nectarous glands* (*nectaries*).—Number, arrangement: Four spherical nectarous glands borne on and along hair-like stems emerging from base of bracts and arranged around the female flower pedicel.

*Nectary surface*.—Glabrous, glossy.

*Nectaries colors*.—Either N144A or 183A.

*Lastingness of cyathium on plant*.—An individual cyathium lasts from 10 to 15 days on an individual plant.

*Lastingness of cyathium* (*when removed from plant*).—Cyathium lasts an average of 24 hours when removed from plant.

*Cyathium fragrance*.—None observed.

Female Flowers and Reproductive Organs:

*Position*.—Solitary flower whose pedicel emerges from the center of the bract bases.

*Pedicel*.—Dimensions: 3 mm.-5 mm. in length, 1.0-1.5 mm in diameter. Color: 155C. Texture: Soft and flexible. Shape: Cylindrical. Surface: Puberulent.

*Pistil*.—1 in number. Dimensions: 3 mm. in length, 1 mm. in width, Color: 144A.

*Style*.—1 in number. Dimensions: 1 mm. in length and 0.1 mm. in width Color: N144A.

*Stigma*.—3 in number, longitudinally fused. Dimensions: Tiny, less than 0.5 mm. in length or diameter. Color: N144D.

*Ovary*.—Ovary shape: Ellipsoidal, five-parted Locules (carpels): 5 Ovary surface: Pubescent. Ovary dimensions: 1.50 mm. in width and 1.50 mm. in height. Ovary color: 144A. Ovary position: Superior.

Male flowers and Reproductive Organs: Male flowers emerge around base of female flower as female flower ages and bends away.

*Pedicel*.—Dimensions: 3 mm.-5 mm. in length, 1.0-1.5 mm in diameter. Color: 155C. Shape: Cylindrical. Surface: Puberulent.

*Stamens*.—3-4 in number.

*Stamen dimensions*.—1 mm.-2 mm. in length and less than 0.5 mm. in diameter.

*Anther dimensions*.—0.50 mm. in length and approximately 0.25 mm. in width.

*Anther shape*.—Bifid.

*Anther color*.—20A.

*Pollen color*.—No pollen has been observed.

Seed: No seed has been observed to date.

COMPARISON OF 'WALEULITR' WITH ITS SPORT PARENT VARIETY 'WALEUTINY' AND WITH OTHER COMMERCIAL VARIETIES

'WALEULITR' is distinguishable from the parent plant 'WALEUTINY' by foliage color, as follows. The foliage of 'WALEUTINY' is uniformly green throughout the season. The foliage of 'WALEULITR' is mid-green in color in late spring, becoming golden and then bronze in color in late summer and early fall.

'WALEULITR' may also be distinguished from plants of its species *Euphorbia* x *martinii*, which is widely available in commerce. The foliage of *Euphorbia* x *martinii* is entirely grey-green in color.

A widely available variety of *Euphorbia* x *martinii* is 'Ascot Rainbow' (U.S. Plant Pat. No. 21,401). Whereas the foliage of 'WALEULITR' is either green or gold or bronze in color as the season progresses, it is not a variegated variety. 'Ascot Rainbow' bears variegated foliage with yellow margins and bears variegated bracts.

In summary, in comparison with its sport parent and with other varieties of the species *Euphorbia* x *martinii*, 'WALEULITR' exhibits novel lighter and brighter foliage color changes throughout the growing season.

I claim:

1. A new and distinct cultivar of *Euphorbia* plant named 'WALEULITR' as described and illustrated.

* * * * *